US009951100B2

(12) United States Patent
Yang et al.

(10) Patent No.: US 9,951,100 B2
(45) Date of Patent: *Apr. 24, 2018

(54) METHOD FOR ISOLATING AND PURIFYING RECOMBINANT HUMAN SERUM ALBUMIN FROM TRANSGENIC RICE GRAIN

(71) Applicant: Healthgen Biotechnology Co., Ltd., Wuhan, Hubei (CN)

(72) Inventors: Daichang Yang, Hubei (CN); Yang He, Hubei (CN); Guangfei Li, Hubei (CN); Jingru Liu, Hubei (CN)

(73) Assignee: HEALTHGEN BIOTECHNOLOGY CO., LTD., Wuhan, Hubei (CN)

( * ) Notice: Subject to any disclaimer, the term of this patent is extended or adjusted under 35 U.S.C. 154(b) by 19 days.

This patent is subject to a terminal disclaimer.

(21) Appl. No.: 14/676,727

(22) Filed: Apr. 1, 2015

(65) Prior Publication Data

US 2015/0203530 A1 Jul. 23, 2015

Related U.S. Application Data

(63) Continuation of application No. 13/206,884, filed on Aug. 10, 2011, now Pat. No. 9,023,990.

(30) Foreign Application Priority Data

Dec. 24, 2010 (CN) .......................... 2010 1 0606635

(51) Int. Cl.
*B01J 20/00* (2006.01)
*C07K 14/765* (2006.01)
*C07K 1/18* (2006.01)
*B01J 20/32* (2006.01)
*A61K 38/00* (2006.01)

(52) U.S. Cl.
CPC ............. *C07K 1/18* (2013.01); *B01J 20/3285* (2013.01); *C07K 14/765* (2013.01)

(58) Field of Classification Search
None
See application file for complete search history.

(56) References Cited

U.S. PATENT DOCUMENTS

| | | | |
|---|---|---|---|
| 2,705,230 A | 3/1955 | Reid | |
| 4,446,163 A | 5/1984 | Galle et al. | |
| 4,754,019 A | 6/1988 | Gion et al. | |
| 5,459,048 A * | 10/1995 | Kuner | G01N 33/56911 424/168.1 |
| 5,521,287 A * | 5/1996 | Ohmura | C07K 14/765 530/363 |
| 5,561,115 A * | 10/1996 | Tenold | C07K 14/765 530/362 |
| 5,612,196 A | 3/1997 | Becquart | |
| 7,193,041 B2 * | 3/2007 | Perry | B01D 15/3828 530/344 |
| 7,304,208 B2 | 12/2007 | Rodriquez et al. | |
| 7,423,124 B2 * | 9/2008 | Belew | C07K 14/765 530/364 |
| 8,058,407 B2 * | 11/2011 | Sun | B01D 15/3847 424/177.1 |
| 9,255,138 B2 | 9/2016 | Yang et al. | |
| 2001/0034053 A1 * | 10/2001 | Winge | C07K 14/8128 435/212 |
| 2002/0127661 A1 * | 9/2002 | Farwick | C07K 14/34 435/106 |
| 2003/0170810 A1 * | 9/2003 | Vedadi | B01D 15/361 435/69.1 |
| 2005/0214902 A1 * | 9/2005 | Belew | C07K 14/765 435/69.1 |
| 2007/0293420 A1 * | 12/2007 | Schumann | C07K 14/505 530/412 |
| 2008/0206436 A1 | 8/2008 | Strohbehn et al. | |
| 2008/0318277 A1 * | 12/2008 | Huang | A23L 1/1041 435/70.1 |
| 2009/0105465 A1 * | 4/2009 | Arunakumari | A61K 39/39525 530/416 |

(Continued)

FOREIGN PATENT DOCUMENTS

| | | |
|---|---|---|
| CN | 1896239 | 1/2007 |
| CN | 100540667 | 9/2009 |

(Continued)

OTHER PUBLICATIONS

Mavituta, A.M. (2005) Production of recombinant Human Serum Albumin in transgenic plants and plant cells, Dissertation, Doktorin der Naturwissenschaften, pp. 1-143.*
Belew et al. (2008) Purification of Recombinant Human Serum Albumin (rHSA) Produced by Genetically Modified Pichia Pastoris, Separat. Sci. Technol., vol. 43, pp. 3134-3153.*
"HIC" (2005) Macro-Prep HIC support, pp. 1-2.*
Bio-Rad (2010) BioProcess, //www.bioprocessintl.com/ journal/ 2010/July_August/ Nuvia-S-Media, pp. 1-4.*
Belew et al., "Purification of recombinant human serum albumin (rHSA) produced by genetically modified Pichia Pastoris," Separ Sci Tech (2008) 43:3134-3153.
BIO-RAD BioProcess International (2010), http://www.bioprocessintl.com/journal/2010/July_August/Nuvia-S-Media, retreived from Internet May 10, 2013, 4 pages.

(Continued)

*Primary Examiner* — Manjunath N Rao
*Assistant Examiner* — Samuel W Liu
(74) *Attorney, Agent, or Firm* — Morrison & Foerster LLP

(57) ABSTRACT

A method for separating and purifying recombinant human serum albumin (rHSA) from transgenic rice grain, sequentially comprising the steps of: 1) subjecting crude extract of rHSA to cation exchange chromatography to obtain primary product I; 2) subjecting the primary product I to anion exchange chromatography to obtain secondary product II; 3) subjecting the secondary product II to hydrophobic chromatography to obtain purified rHSA. The method may further comprise a step of ceramic hydroxyapatite chromatography prior to the hydrophobic chromatography. The method has the advantages of low cost and easy operation. The resultant rHSA has a purity of about 99% by HPLC.

23 Claims, 10 Drawing Sheets

(56) References Cited

U.S. PATENT DOCUMENTS

| | | | |
|---|---|---|---|
| 2010/0031394 A1 | 2/2010 | Huang et al. | |
| 2010/0047428 A1* | 2/2010 | Lejars | C07K 1/303 426/580 |
| 2010/0190708 A1* | 7/2010 | Tsuno | A61K 38/168 514/21.2 |
| 2012/0315697 A1 | 12/2012 | Pettit et al. | |
| 2015/0329618 A1 | 11/2015 | Yang et al. | |
| 2016/0122414 A1 | 5/2016 | Yang et al. | |

FOREIGN PATENT DOCUMENTS

| | | |
|---|---|---|
| CN | 101665798 | 3/2010 |
| CN | 101768206 | 7/2010 |
| CN | 102127164 | 7/2011 |
| CN | 102190722 | 9/2011 |
| CN | 102532254 | 7/2012 |
| CN | 103880947 | 1/2016 |
| EP | 0 428 758 | 5/1991 |
| EP | 0 683 233 | 5/1995 |
| WO | WO-90/15617 | 12/1990 |
| WO | WO-2000/044772 | 8/2000 |
| WO | WO-2004/099405 | 11/2004 |
| WO | WO-2012/083580 | 6/2012 |
| WO | WO 2012083580 A1 | 6/2012 |

OTHER PUBLICATIONS

Cabrera-Crespo et al., "Albumin purification from human placenta," Biotechnol Appl Biochem (2000) 31:101-106.
Chen et al., "Purification of recombinant human serum albumin from fermentation broth," Pharm Biotechnol (2003) 10(1):25-27 (English language abstract).
Englard et al., "Precipitation Techniques," Method in Enzymology (1990) 182:285-300.
Hegyi et al., Introduction to Practical Biochemistry (2013), pp. 1-2, 89-104.
Huang et al., "Production of human serum albumin by sugar starvation induced promoter and rice cell culture," Transgenic Res (2005) 14(5):569-581.
Latta et al., "Synthesis and purification of mature human serum albumin from E. coli," Biotechnology (1987) 5:1309-1314.
Macro-Prep® HIC Support product information, 2 pages.
Mavituna "Production of recombinant human serum albumin in transgenic plants and plant cells," Dissertation, Doktorin der Naturwissenschaften (2005), pp. 1-143.
SAFC Biosciences, "Protein Purification Techniques," (2006) 1:1-2.
Saunders et al., "Secretion of human serum albumin from Baillus subtilis," J. of Bateriology (1987) 169(7):2917-2925.
Advisory Action for U.S. Appl. No. 13/206,884, dated Feb. 25, 2014, 4 pages.
Final Office Action for U.S. Appl. No. 13/206,884, dated Oct. 25, 2013, 25 pages.
Final Office Action for U.S. Appl. No. 13/206,844, dated Dec. 27, 2013, 17 pages.
Issue Fee Payment for U.S. Appl. No. 13/206,884, filed Apr. 1, 2015, 3 pages.
Notice of Allowance for U.S. Appl. No. 13/206,884, dated Jan. 2, 2015, 10 pages.
Notice of Allowance for U.S. Appl. No. 13/206,844, dated Oct. 1, 2015, 7 pages.
Office Action for U.S. Appl. No. 13/206,884, dated May 22, 2013, 19 pages.
Office Action for U.S. Appl. No. 13/206,844, dated Jul. 16, 2013, 9 pages.
Office Action for U.S. Appl. No. 13/206,844, dated Aug. 27, 2014, 20 pages.
Office Action for U.S. Appl. No. 13/206,844, dated Jun. 4, 2015, 18 pages.
Request for Continued Examination in U.S. Appl. No. 13/206,884, filed Apr. 25, 2014, 42 pages.
Request for Continued Examination in U.S. Appl. No. 13/206,844, filed Apr. 28, 2014, 13 pages.
Response to Final Office Action in U.S. Appl. No. 13/206,884, filed Jan. 27, 2014, 24 pages.
Response to Office Action in U.S. Appl. No. 13/206,884, filed Aug. 22, 2013, 27 pages.
Response to Office Action for U.S. Appl. No. 13/206,844, filed Oct. 16, 2013, 7 pages.
Response to Office Action for U.S. Appl. No. 13/206,844, filed Feb. 26, 2015, 15 pages.
Response to Office Action for U.S. Appl. No. 13/206,844, filed Sep. 4, 2015, 6 pages.
International Preliminary Report for PCT/CN2013/075405, dated Apr. 13, 2015, 15 pages (English translation included).
International Search Report for PCT/CN2013/075405, dated Sep. 26, 2013, 7 pages (English translation included).
GE Healthcare Capto MMC multimedia product sheets 2005: 24 pages.
Lees, A., et al. 2009 BioProcess International: 42-48, 5 pages.
He, Y., et al. 2011 PNAS 108(47): 19078-19083, and Supporting Information p. 1-8.
Non-final Office Action in U.S. Appl. No. 14/653,258, dated Jun. 27, 2017, 16 pages.

* cited by examiner

METHOD FOR ISOLATING AND PURIFYING RECOMBINANT HUMAN SERUM ALBUMIN FROM TRANSGENIC RICE GRAIN

CROSS-REFERENCE TO RELATED APPLICATIONS

This application is a continuation of U.S. patent application Ser. No. 13/206,884, now allowed, which claims the priority of Chinese Application No. 201010606635.8, filed on Dec. 24, 2010. The contents of the above applications are hereby incorporated by reference in their entireties.

FIELD OF THE INVENTION

The present invention relates to biotechnology, and particularly to a method for isolating and purifying recombinant human serum albumin (rHSA) from transgenic rice grain on a large scale.

BACKGROUND OF THE INVENTION

Human serum albumin (HSA) is a single chain, non-glycosylated protein consisting of 585 amino acids, having a molecular weight of 66.5 kD and an isoelectric point between 4.7~4.9. It is the most abundant protein in human blood plasma, making up about 60% of the total plasma proteins. There is about 40 g of HSA in per liter of human blood. Besides being present in the plasma, HSA is also found in tissues and body secretions, skins and lymph cavities. Under normal physiological conditions, HSA has an effect of maintaining plasma colloid osmotic pressure, nourishing, accelerating concrescence of wounds, and as a carrier, participating in transportation of many hydrophobic biological molecules such as hormones, biological active substances and drugs in the blood. Therefore, HSA is an important medical protein that is mainly used clinically for treatment of hypoproteinemia caused by loss of blood, burn, scald, plastic surgery and brain lesion, as well as for treatment of liver cirrhosis, hydronephrosis and so on. At present, HSA for clinical use is mainly prepared by extracting and isolating from human plasma. However, this preparation approach has the following disadvantages: on one hand, the source of plasma is insufficient, i.e. the limited blood supply is unable to meet the demands of production of HSA and the relevant preparations thereof; on the other hand, blood itself may potentially be a risk factor, for example it may contain dangerous infectious pathogens such as hepatitis virus, human immunodeficiency virus (HIV) and so on, which causes enormously concerns about the application of HSA extracted from plasma. Therefore, it is urgent to develop an alternative process to produce HSA.

With the development of modern DNA recombinant and synthesis techniques, researchers take a profound interest in the production and application of recombinant human serum albumin (rHSA). So far, various expression systems have been experimentally used for mass production of rHSA. For example, prokaryotes such as colon *bacillus* (Latta, M. et al., Bio/Technology, 5:1309-1314, (1987)), *bacillus subtilis* (Saunders, C. W. et al, J. Bacteriol. 169: 2917-2925, (1987)), eukaryotes such as yeasts (WO 00/44772, EP0683233A2, U.S. Pat. No. 5,612,196) and also cultivation of animal cells have been used for the production of rHSA. However, such approaches supra are not suitable for industrialized production either due to low expression level or high production cost. Chinese patent application No. 200510019084.4 of the present inventors discloses a method for producing rHSA using rice endosperm cells as bioreactor, comprising: using promoters and signal peptides specifically expressed in rice endosperm to mediate the entry of rHSA into endomembrane system of the endosperm cells of rice and store rHSA in the protein bodies of the rice endosperm, thus allowing rHSA to accumulate extensively in the rice grain and reach a higher expression level finally. The expression level of the obtained rHSA is at least above 0.3% based on the weight of the rice grain. The method has the advantages of high expression level and low cost, thereby it provides the possibility to develop a novel strategy for the production of protein drugs.

The rHSA produced by any expression system should be purified before entering market. The purification technique may affect the quality of the product as well as production cost. The cost of purification process makes up about 80~90% of the total production cost. At present, there is no purification process for separating and purifying rHSA from rice grain. Therefore, it is technically difficult and economically risky to develop a simple and cost-effective purification process to purify rHSA from rice grain.

At present, the techniques for extracting rHSA from yeast and plant suspension cells have been reported. For example, Chinese patent application CN101768206A disclosed a process for purifying rHSA expressed in Pichia pastoris, comprising: filtrating the fermentation broth of rHSA with a ceramic membrane, and sequentially subjecting the filtrate to cation exchange chromatography, hydrophobic chromatography and weak anion exchange chromatography to obtain purified rHSA. However, due to the substantial differences of the impurities among the rice grain, yeast and plant suspension cells, those prior art can not be directly used for separating and purifying rHSA from rice grain. Therefore, it is desirable to develop a simple and effective process for separating and purifying rHSA from rice grain to produce rHSA with high yield and high purity, which would provide a basis for future industrialized production.

SUMMARY OF THE INVENTION

The object of the present invention is to provide a method for separating and purifying recombinant human serum albumin (rHSA) from rice grain on a large scale.

To achieve the above object, the present invention provides the following technical solutions:

A method for separating and purifying recombinant human serum albumin from rice grain, sequentially comprising the steps of:
1) subjecting crude extract of recombinant human serum albumin to cation exchange chromatography to obtain primary product I;
2) subjecting the primary product I to anion exchange chromatography to obtain secondary product II;
3) subjecting the secondary product II to hydrophobic chromatography to obtain purified recombinant human serum albumin.

In step 1), the cation exchange chromatography may be performed on a strong cation chromatography resin as chromatography media, which is selected from the group consisting of UNO Sphere S, Nuvia. S, Capto MMC, MacroPrep-CM. UNO Sphere S or Capto MMC is preferred.

The cation exchange chromatography may employ pH gradient elution or NaCl concentration gradient elution. The pH gradient elution is preferred.

In an embodiment, elution buffer for cation exchange chromatography comprises acetate buffer, 0.25M sodium chloride, with a pH of 5.2.

In step 2), the anion exchange chromatography may be performed on a strong anion chromatography resin as chromatography media, which is selected from the group consisting of UNOsphere Q, Q Sepharose FF ("FF" stands for "fast flow") and DEAE Sepharose FF. Q Sepharose FF is preferred.

In an embodiment, elution buffer for anion exchange chromatography comprises phosphate buffer, 0.2M sodium chloride, with a pH of 7.5.

In step 3), the hydrophobic chromatography may be performed on a chromatography media selected from the group consisting of Phenyl sepharose HP, Phenyl sepharose FF, macro-prep t-butyl and macro-prep methyl. Phenyl sepharose HP is preferred.

The eluate containing the target protein from hydrophobic chromatography column can be prepared into finished product by known techniques such as ultra-filtration concentration and freeze-drying.

Further, the method may comprise a step of subjecting the secondary product II to Macro-prep ceramic hydroxyapatite chromatography prior to the hydrophobic chromatography of said step 3). That is to say, in such an embodiment, the secondary product containing the target protein was subjected to Macro-prep ceramic hydroxyapatite chromatography as step 3) and then hydrophobic chromatography to obtain purified target protein as step 4).

The ceramic hydroxyapatite chromatography may be performed on a chromatography media selected from the group consisting of Macro-prep ceramic hydroxyapatite Type I and Macro-prep ceramic hydroxyapatite Type II. Macro-prep ceramic hydroxyapatite type I is preferred.

In an embodiment, the loading buffer employed in cation exchange chromatography comprises acetate buffer, with a pH below 5.0.

An elution buffer for eluting the target protein employed in cation exchange chromatography may comprise either acetate buffer and sodium chloride, or phosphate buffer and sodium chloride, with a pH of 5.0~6.7. Preferably, the concentration of sodium chloride is 0.25M and the pH of the elution buffer is 5.2.

In one embodiment, the cation exchange chromatography is performed on UNO Sphere S or Capto MMC, and the elution buffer comprising acetate buffer, 0.25M sodium chloride, with a pH of 5.2 or 6.7 is employed.

In one embodiment, the cation exchange chromatography is performed on nuvia S as chromatography media, and an elution buffer comprising acetate buffer, 0.25M sodium chloride, with a pH of 5.0 or 5.2 is employed.

In one embodiment, the cation exchange chromatography is performed on Capto MMC as chromatography media, and a washing buffer comprising acetate buffer, 1M sodium chloride, with a pH of 4.7 is employed to remove impurities; and an elution buffer comprising phosphate buffer, 1M sodium chloride, with a pH of 6.7 is employed to elute the target protein.

In one embodiment, the cation exchange chromatography is performed on MacroPrep-CM as chromatography media, and a washing buffer comprising acetate buffer, 1M sodium chloride, with a pH of 4.7 is employed to remove impurities; and an elution buffer comprising phosphate buffer, 0.1M sodium chloride, with a pH of 6.5 is employed to elute the target protein.

In one embodiment, the anion exchange chromatography is performed on Q Sepharose FF as chromatography media, and an elution buffer comprising phosphate buffer, 0.25M sodium chloride with a pH of 6.0~7.0 is employed.

In one embodiment, the anion exchange chromatography is performed on DEAE sepharose FF as chromatography media, and a washing buffer comprising phosphate buffer, 0.1 M sodium chloride with a pH of 6.0~7.0 is employed to remove impurities; and an elution buffer comprising phosphate buffer, 0.25M sodium chloride with a pH of 6.0~7.0 is employed to elute the target protein.

In one embodiment, the rHSA-containing fraction to be purified by hydrophobic chromatography may further comprise ammonia sulfate. The concentration of ammonia sulfate may be from 0.1M to 1M.

In one embodiment, the hydrophobic chromatography is performed on Phenyl sepharose HP as chromatography media, and the concentration of ammonia sulfate in the rHSA-containing fraction to be purified is 0.4M.

In one embodiment, the hydrophobic chromatography is performed on Phenyl sepharose FF as chromatography media, and the concentration of ammonia sulfate in the rHSA-containing fraction to be purified is 0.1M.

In one embodiment, the hydrophobic chromatography is performed on MacroPrep-t-Butyl as chromatography media, and the concentration of ammonia sulfate in the rHSA-containing fraction to be purified is from 0.6M to 1.0M.

In one embodiment, the Macro-prep ceramic hydroxyapatite chromatography employs an elution buffer comprising phosphate buffer with a pH of 7.0~7.5 to elute the target protein.

Said rHSA of the present invention can be prepared using endosperm cells of rice as bioreactor, which is disclosed in Chinese patent application No. 200510019084.4 filed by the present applicant. The rHSA expressed in the transgenic rice can be extracted by the method disclosed in Chinese patent application No. 201010597544.2 filed by the present applicant, which preferably comprises the steps of:

i) mixing milled transgenic rice containing rHSA with an extraction buffer in w/v (kg/l) ratio of 1:5, followed by extracting for 1~1.5 hours at 55~60° C. to obtain a mixture I; the extraction buffer comprises 10~30 mM phosphate buffer, 10~20 mM sodium acetate, 15~30 mM ammonia sulfate and 5~20 mM sodium caprylate, with a pH of 6.5~8;

ii) adjusting pH of the mixture I of step i) to 4.0~4.5 and precipitating it for 3~12 hours to obtain mixture II;

iii) filtrating the mixture II of step ii) to remove starches or non-target proteins, and then collecting the filtrate to obtain a crude extract containing high concentration of rHSA.

In one embodiment, said filtrating comprising steps of filtrating by pressure filtration with a filter cloth type plate-frame filter, then filtrating by micro-filtration with a polyethersulfone hollow fiber membrane. The hollow fiber membrane has a pore size of 0.20 μm~0.45 μm, preferably 0.22 μm.

The technical solutions according to the present invention have the following advantages:

1. In respect to relatively high content of pigments and polysaccharides in rice grain, cation exchange chromatography is used as the first step in the present invention to effectively enhance the loading capacity for capturing or binding rHSA, which increases the chromatographic efficiency. In contrast, if anion exchange chromatography is used as the first step, the loading capacity for capturing rHSA is only about 20% of the theoretical capacity. Meanwhile, both UNO Sphere S and Capto-MMC have characters of excellent stability and a long lifetime even in sodium hydroxide, which extends the depreciation period of the chromatography media and simplifies the sanitization operation in the present invention, and finally reduces the cost of the target product.

2. Anion exchange chromatography is used as the second step in the present invention. After optimizing the elution conditions, above 80% of the non-target proteins in rice grain could be removed, thereby effectively eliminating the non-target proteins and recovering rHSA. Since the pigments and polysaccharides have been removed from the rice grain in the first step by cation exchange chromatography, their influence on loading capacity and purification efficiency in the anion exchange chromatography has been eliminated.

3. Macro-prep ceramic hydroxyapatite chromatography is used as the third step in the present invention to eliminate the dimer and polymers because of more dimers or polymers could cause allergenic when rHSA is used as injection medicine. This step improves markedly the purity, which meets the requirement of high purity for clinical application or more.

4. Hydrophobic chromatography is used as the final step in the present invention. After the three-step chromatographic procedure, the HPLC purity of the target product can reach about 99.0%.

Figure 1:
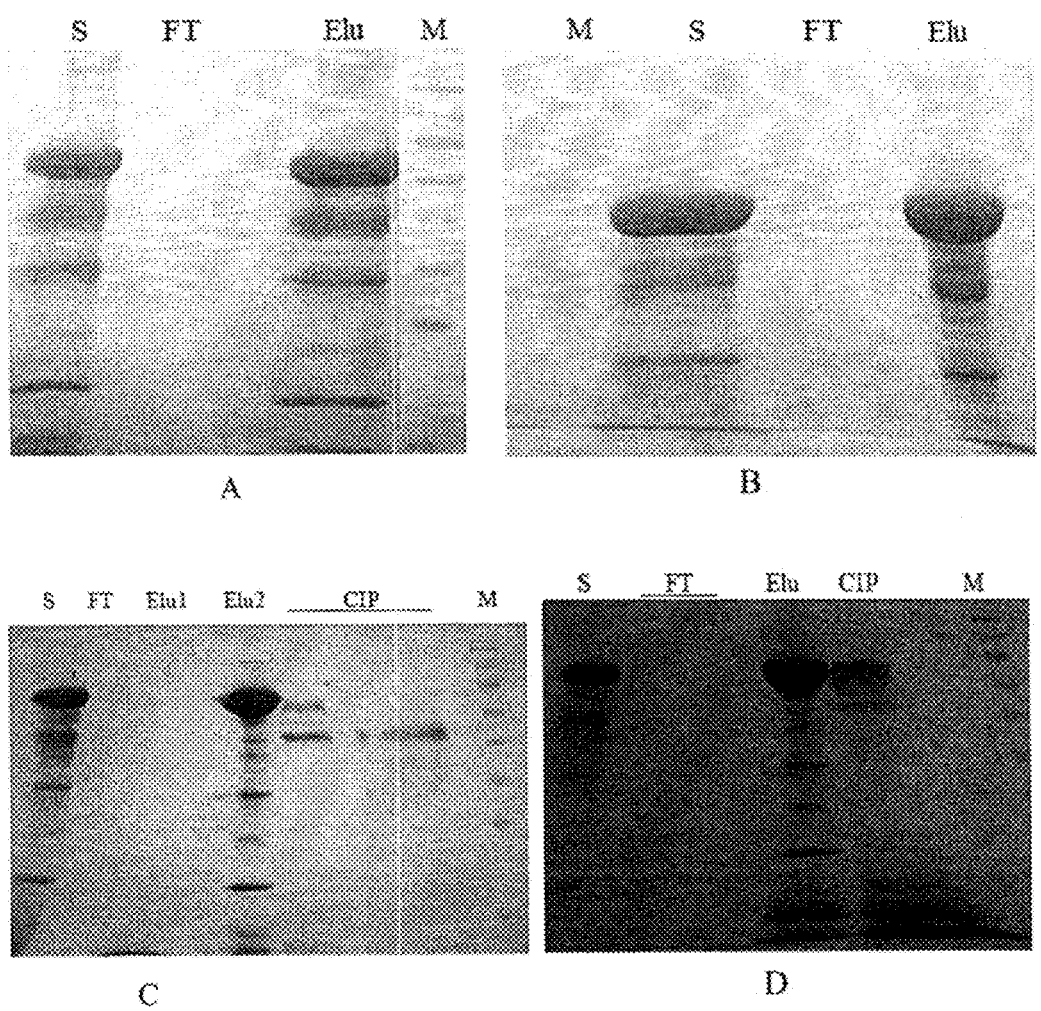
FIG. 1 is an image of SDS-PAGE of fractions obtained from cation exchange chromatography performed on different chromatography media as primary purification, wherein A: UNOsphere S media, B: Nuvia S media, C: Capto MMC media and D: MacroPrep-CM media.

In the above figures, S: loading sample, FT: transmission fluid, Elu: the rHSA-containing eluate, Elu 1: non-target protein eluate, Elu 2: rHSA eluate, CIP: cleaning-in-place fraction.

DETAILED DESCRIPTION OF THE INVENTION

The features and advantages of the present invention can be further understood from the following examples. The examples are illustrative only and should not to be construed as limiting the invention in any way.

Selection of Chromatography Media and Elution Conditions in Cation Exchange Chromatography The present invention defines the chromatography media of a cation exchange resin as having a high working flow rate, including UNO Sphere S, Nuvia S, Capto MMC and etc. manufactured by Bio-RAD.

It is found by experiments that each of Capto MMC, Nuvia S and UNO Sphere S can be used for purification of rHSA. Capto MMC has the best effect on the protein purification, followed by UNO Sphere S and Nuvia S. There are no significant difference between the effects on protein purification of Nuvia S and UNO Sphere S. However, under the same working flow rate conditions, the loading capacity of UNO Sphere S is 1.5 times larger than that of Capto MMC; UNO Sphere S has a same working flow rate as Capto MMC; UNO Sphere S has excellent stability even in high concentration of sodium hydroxide and has better cleaning process, longer working lifetime and lower cost in comparison to Capto MMC.

Nuvia S and UNO Sphere S have similar properties but have difference in extention of ligands and matrix particle sizes. Under their respective optimal working flow rate, the loading capacity of Nuvia S is 1.4 times larger than that of UNO Sphere S; however, the working flow rate of Nuvia S is about a half smaller than that of UNO Sphere S. Instead, UNO Sphere S has larger loading capacity than Nuvia S at the same flow rate, and both of them have almost equivalent purification capability.

In view of the various factors, UNO Sphere S is preferably used as chromatography media for cation exchange chromatography.

The rHSA-containing extract is loaded on a column packing UNO Sphere S at a relatively low pH (pH=4.4) to ensure that rHSA can be completely absorbed on the media, and then eluted by pH gradient elution buffers and NaCl gradient elution buffers respectively to learn the basic elution conditions.

The results suggests that in pH gradient elution, the rHSA absorbed on the UNO Sphere S column is slightly desorbed when the pH of the elution buffer is above 5.5, indicating that the pH of loading buffer should not be higher than 5.5; when the pH of the elution buffer is 5.68, rHSA is completely desorbed from the column. Thus rHSA on the UNO Sphere S column is very sensitive to pH gradient elution.

In NaCl concentration gradient elution, the target protein rHSA is desorbed when the concentration gradient is from 35% to 60% 1M sodium chloride (NaCl), thus indicating that rHSA on the UNO Sphere S column is not sensitive to NaCl concentration gradient elution. The results demonstrate that both pH gradient and NaCl gradient can be used to elute the rHSA. Moreover, pH gradient elutes rHSA with more sensitivity and smaller volume of elution buffer. In contrast, NaCl gradient can not easily elute the rHSA, and requires high concentration of NaCl and larger volume of elution buffer. Considering from purification efficiency and recovery rate, the preferred elution buffer is a phosphate buffer (pH 5.2) containing 0.25M NaCl.

Selection of Chromatography Media and Elution Conditions for Anion Exchange Chromatography Like a cation exchange resin, an anion exchange resin can also be used for purification of rHSA. The present invention defines the chromatography media of an anion exchange resin as having a high flow rate and a high loading capacity, including UNOsphere Q, Q Sepharose FF, DEAE sepharose FF and etc.

It is found by experiments that each of UNOsphere Q, Q Sepharose FF and DEAE sepharose FF can be used for purification of rHSA. UNOsphere Q has a faster flow rate than Q Sepharose FF, but Q Sepharose FF has better purification efficiency than UNOsphere Q; while DEAE Sepharose FF has similar purification efficiency but a slower flow rate compared to Q Sepharose FF.

As described above, as a chromatography media for cation exchange chromatography, UNO-sphere S has a slightly poorer purification capability than Capto MMC. However, it is demonstrated by experiments that this adverse effect can be eliminated by the improvement of systematic purification capability. UNO-sphere S will not cause adverse effect on the subsequent anion exchange chromatography. In a preferred embodiment, Q sepharose FF is preferably used as the chromatography media for anion exchange chromatography and the elution buffer for eluting target protein comprises phosphate buffer and 0.2MNaCl, with a pH of 6.8.

Determination of the Order of Anion- and Cation-Exchange Chromatography

Both anion- and cation-exchange chromatography can be used as the primary purification of rHSA, however, it is found by experiments that when Q Sepharose FF anion exchange resin is used in the primary purification step, its loading capacity is far lower than the theoretical capacity. It may be associated with the soluble polysaccharides and nucleic acids largely present in rice grain. Because the soluble polysaccharides and nucleic acids contain negative charges may bind to Q Sepharose FF to reduce its loading capacity. It is demonstrated by experiments that the content of the soluble polysaccharides in rHSA extract can be reduced by dialysis, thereby increasing the loading capacity of Q Sepharose FF.

In contrast, cation exchange chromatography media such as UNO sphere S, Nuvia S and Capto MMC does not bind to the soluble polysaccharides or nucleic acids, avoid causing a decrease in the loading capacity. Therefore, cation exchange chromatography is determined as the primary purification and anion exchange chromatography is determined as the secondary purification in the present invention.

Selection of Chromatography Media for Hydrophobic Chromatography

The present invention employs various hydrophobic chromatography media with the similar properties for the purification step, including Phenyl sepharose HP, Phenyl sepharose FF (LS), macro-prep t-butyl and macro-prep methyl. Phenyl sepharose HP has a strong hydrophobic property and excellent purification capability. The capability to remove the most non-target proteins and other impurities from the crude extract is critical to the purification efficiency; however, there is some inconvenience in the application of this chromatography media due to its fine particle size, low flow rate and special working mode.

Compared to Phenyl sepharose HP, Phenyl sepharose FF (LS) has the same ligand and matrix, but different diameter of the spherical matrix and different density of the ligand. The average particle size of the matrix of Phenyl sepharose FF (LS) is 3 times larger than that of Phenyl sepharose HP, and thus the former has a higher working flow rate. When used in the production of rHSA, it can shorten the production period. MacroPrep-Butyl has a weaker hydrophobicity than both Phenyl sepharose FF and Phenyl sepharose HP, while Macro-prep methyl has an even weaker hydrophobicity than MacroPrep-Butyl. Phenyl sepharose FF is performed experimentally at the same working mode as Phenyl sepharose HP to collect transmission fluid. In the selection of the concentration of salt in the loading sample, when the sample is loaded with an equilibration buffer (25 mM PB, 0.5M $(NH_4)_2SO_4$, pH 6.8) and eluted with 100% water, it is found that more than 50% of rHSA are retained on the column. As a result the salt concentration of the equilibration buffer should be reduced.

The samples filtrated by UNO sphere S and Q sepharose FF column are added with ammonia sulfate to adjust the concentration of ammonia sulfate to 0.2M and 0.1M, respectively prior to loading on a Phenyl sepharose FF (LS) column. The transmission fluid and pure water eluate are collected to perform SDS-PAGE detection. The results show that Phenyl sepharose FF (LS) has stronger hydrophobicity than Phenyl sepharose HP and has better effect to eliminate the non-target proteins in the sample even when the concentration of ammonia sulfate in the loading sample is as low as 0.1M. The product obtained by Phenyl sepharose FF (LS) has a purity of 93.5%. However, still 30% of rHSA is lost on the Phenyl sepharose FF(LS) column. The above experiment is performed using sodium chloride instead of ammonium sulphate, the similar results are obtained. Though the loss of rHSA on the column is reduced, the HPLC purity of the product is still about 93%.

The samples filtrated by UNO sphere S and Q sepharose FF column are added with ammonia sulfate to adjust the concentration of ammonia sulfate to 1M, 0.8M or 0.6M respectively, prior to loading on a macro-prep t-butyl and macro-prep methyl column. The transmission fluid and pure water eluate are collected to perform SDS-PAGE detection. The results show that macro-prep t-butyl and macro-prep methyl has poor hydrophobicity. Both of them have poor purification capability on rHSA, and the obtained rHSA has a purity of 90% by HPLC.

To select which Macro-prep ceramic hydroxyapatite Type I or Type II, we compared two types of Macro-prep ceramic hydroxyapatite from Bio Rad. We found the Macro-prep ceramic hydroxyapatite type I is much better than type II. After Macro-prep ceramic hydroxyapatite type I chromatpgraphy, the monomer content can reach up to 98.998%.

As described above, though the other chromatography media has the advantage of fast working flow rate over Phenyl sepharose HP, they could not achieve the comparable purification efficiency to Phenyl sepharose HP. Phenyl sepharose HP has a relative low working rate, but can ensure that the target protein has a purity of more than 98%. Thus Phenyl sepharose HP is preferably used as the media for hydrophobic chromatography.

EXAMPLES

Materials and Instruments

Filter cloth type plate-frame filter press, type: XMS4/500-UB, manufactured by Shanghai Tianli Filter Press Co., Ltd (China); 0.20 μm hollow fiber column, available from Huzhou Kelu Membrane Technology Co., Ltd. (China);

UNO Sphere S, nuvia S, Capto MMC, MacroPrep-CM, MacroPrep-methyl, MacroPrep-Butyl media, available from BIO-RAD (US);

Q sepharose, Phenyl sepharose HP, Phenyl sepharose FF, DEAE-sepharose FF media, available from GE Healthcare (US);

C10/10, XK16/20 chromatography column, available from GE Healthcare (US)

Biological 15/200 chromatography column, available from BIO-RAD (US)

Example 1: Extraction of rHSA from Transgenic Rice Grain

Transgenic rice could be prepared according to the method disclosed in Chinese patent application No. 200510019084 of the present inventors. The paddy rice was hulled to obtain half-polished rice and then grinded to obtain milled rice with a fineness of 80~100 mesh. The milled rice was mixed with an extraction buffer in a ratio of 1:5 (w/v, kg/L) and extracted for 1.5 hours at 60° C. The extraction buffer comprises 25 mM phosphate buffer, 20 mM sodium acetate, 10 mM ammonium sulfate, 10 mM sodium caprylate, and has a pH of 7.5. The resultant mixture was adjusted to pH 4.5 with acetic acid and placed for at least 3 hours to precipitate non-target proteins. Then the resultant mixture was sequentially subjected to pressure filtration using a plate-frame press filter (filter cloth type) and micro-filtration by hollow fiber column with a pore size of 0.22 μm, to obtain supernatant containing rHSA. The concentration of rHSA was about 0.66 mg/mL.

Example 2: Cation Exchange Chromatography as Primary Purification

1. Cation Exchange Chromatography Performed on UNO Sphere S Media

A XK16/100 column was packed with about 8.7 ml of UNO Sphere S media and equilibrated with 200 ml of equilibration buffer (anhydrous sodium acetate 2 g/L, acetic acid was added to adjust the pH to 4.5) at a flow rate of 300 cm/h until the pH of the effluent was stable. 250 ml of the rHSA extract sample obtained in example 1 was loaded on the column at a flow rate of 600 cm/h. The sample has a conductivity of 6.1 ms/cm and a pH of 4.53. After loading, the sample was eluted with an elution buffer (sodium acetate 2 g/L, acetic acid, pH 5.2, sodium chloride 14.61 g/L) at a flow rate of 300 cm/h. The eluate was collected and viewed by SDS-PAGE to obtain the fractions containing rHSA. The electrophoretogram was shown in FIG. 1A.

2. Cation Exchange Chromatography Performed on Nuvia S Media

A XK16/100 column was packed with about 9.3 ml of Nuvia S media and equilibrated with 200 ml of equilibration buffer (anhydrous sodium acetate 2 g/L, acetic acid was added to adjust the pH to 4.5) at a flow rate of 300 cm/h until the pH of the effluent was stable. 250 ml of the rHSA extract sample obtained in example 1 was loaded on the column at a flow rate of 300 cm/h. The sample has a conductivity of 6.3 ms/cm and a pH of 4.56. After loading, the sample was eluted with an elution buffer (sodium acetate 2 g/L, acetic acid, pH 5.0, sodium chloride 14.61 g/L) at a flow rate of 300 cm/h. The eluate were collected and viewed by SDS-PAGE to obtain the fractions containing rHSA. The electrophoretogram was shown in FIG. 1B.

3. Cation Exchange Chromatography Performed on Capto MMC Media

A XK16/100 column was packed with about 15.1 ml of Capto MMC media and equilibrated with 200 ml of equilibration buffer (anhydrous sodium acetate 2 g/L, acetic acid was added to adjust the pH to 4.5) at a flow rate of 300 cm/h until the pH of the effluent was 4.5 and stable. 250 ml of the rHSA extract sample obtained in example 1 was loaded on the column at a flow rate of 600 cm/h. The sample has a conductivity of 6.3 ms/cm and a pH of 4.56. After loading, the sample was eluted with elution buffer (sodium acetate 2 g/L, acetic acid, pH 4.7, sodium chloride 58.44 g/L) at a flow rate of 300 cm/h to remove impurities and then eluted with elution buffer (sodium dihydrogen phosphate 0.3 g/L, disodium hydrogen phosphate 3.5 g/L, sodium chloride 58.44 g/L, pH 6.7) to obtain the rHSA-containing fractions. The electrophoretogram was shown in FIG. 1C.

4. Cation Exchange Chromatography Performed on MacroPrep-CM Media

A XK16/100 column was packed with about 10 ml of MacroPrep-CM media and equilibrated with 300 ml of equilibration buffer (anhydrous sodium acetate 2 g/L, acetic acid was added to adjust the pH to 4.5) at a flow rate of 200 cm/h until the pH of the effluent was 4.5 and stable. 250 ml of the rHSA extract sample obtained in example 1 was loaded on the column at a flow rate of 300 cm/h. The sample has a conductivity of 6.3 ms/cm and a pH of 4.56. After loading, the sample was washed with washing buffer (sodium acetate 2 g/L, acetic acid, pH 4.7, sodium chloride 58.44 g/L) at a flow rate of 200 cm/h to remove impurities and then eluted with elution buffer (sodium dihydrogen phosphate 0.3 g/L, disodium hydrogen phosphate 3.5 g/L, sodium chloride 5.84 g/L, pH 6.5) to obtain the rHSA-containing fractions. The electrophoretogram was shown in FIG. 1D.

5. Comparison of the Loading Capacity Between Nuvia S Media and UNO Sphere S Media Two XK16/100 columns were packed with about 5 ml of Nuvia S and UNO Sphere S media respectively and equilibrated with 200 ml of equilibration buffer (anhydrous sodium acetate 2 g/L, acetic acid was added to adjust the pH to 4.5) at a flow rate of 300 cm/h until the pH of the effluent was 4.5. The rHSA extract sample obtained in example 1 was loaded on the Nuvia S column and UNO Sphere S column at a flow rate of 300 cm/h, respectively. Absorption value of UV280 during the sample loading was recorded until the absorption value beyond plateau by 10%. The sample volume was recorded and the actual loading capacity per milliliter of Nuvia S or UNO Sphere S at a flow rate of 300 cm/h was calculated, respectively.

Figure 2:
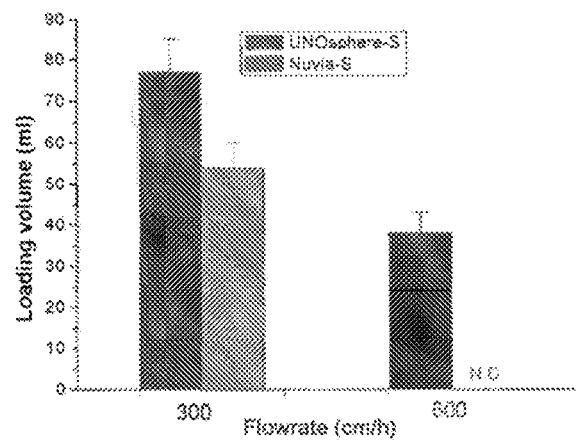
FIG. 2 shows a comparison diagram of the loading capacity (volume) for the rHSA extract between Nuvia S media and UNO Sphere S media at different flow rate (300 cm/h, 600 cm/h).

Further, the UNO Sphere S column was equilibrated with equilibration buffer (anhydrous sodium acetate 2 g/L, acetic acid was added to adjust the pH to 4.5) at a flow rate of 300 cm/h until the pH of the effluent was 4.5. The rHSA extract obtained in example 1 was loaded on the UNO Sphere S column at a flow rate of 600 cm/h and absorption value of UV280 during the sample loading was recorded until the absorption value beyond plateau by 10%. The sample volume was recorded and the actual loading capacity per milliliter of UNO Sphere S at a flow rate of 600 cm/h was calculated. The comparison of loading capacity was shown in FIG. 2.

Example 3: Anion Exchange Chromatography as Primary Purification

1. Anion Exchange Chromatography Performed on UNO Sphere Q Media

Figure 3A:
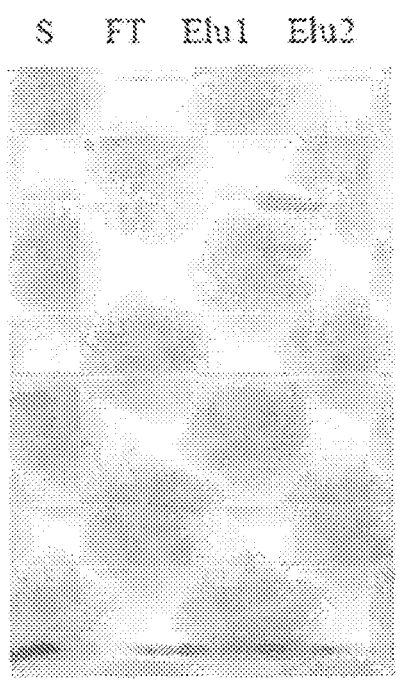
FIG. 3 is an image of SDS-PAGE of fractions obtained by anion exchange chromatography performed on different chromatography media as primary purification, wherein A: UNO Sphere Q media, B: Q Sepharose FF media.

A Biological 15/200 column was packed with about 10 ml of UNO Sphere Q media and equilibrated with 200 ml of equilibration buffer (sodium dihydrogen phosphate 0.3 g/L, disodium hydrogen phosphate 3.5 g/L, sodium hydroxide or hydrochloric acid was added to adjust the pH to 7.5) at a flow rate of 300 cm/h until the pH of the effluent was 7.5. 250ml of the rHSA extract sample obtained in example 1 was adjusted to pH 7.5 and diluted with the buffer until the conductivity was less than 10.0 ms, and then loaded on the UNO Sphere Q column at a flow rate of 300 cm/h. The sample was washed with washing buffer (sodium dihydrogen phosphate 0.3 g/L, disodium hydrogen phosphate 3.5 g/L, sodium chloride 11.68 g/L) to remove impurities and then eluted with elution buffer (sodium dihydrogen phosphate 0.3 g/L, disodium hydrogen phosphate 3.5 g/L, sodium chloride 23.36 g/L) to collect the rHSA-containing fractions. The electrophoretogram was shown in FIG. 3A.

2. Anion Exchange Chromatography Performed on Q Sepharose FF Media

Figure 3B:
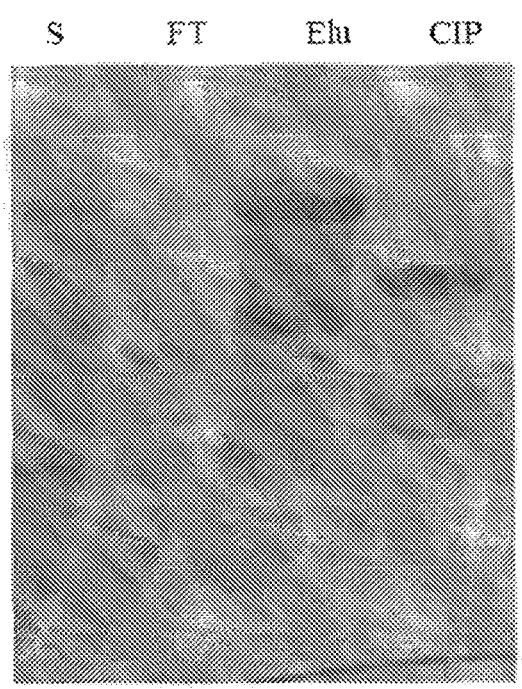

A Biological 15/200 column was packed with about 10 ml of Q Sepharose FF media and equilibrated with 200 ml of equilibration buffer (sodium dihydrogen phosphate 0.3 g/L, disodium hydrogen phosphate 3.5 g/L, sodium hydroxide or hydrochloric acid was added to adjust the pH to 7.0) at a flow rate of 300 cm/h until the pH of the effluent was 7.0. 250 ml of the rHSA extract sample obtained in example 1 was adjusted to pH 6.8 and diluted with the buffer until the conductivity was less than 10.0 ms/cm, and then loaded on the Q Sepharose FF column at a flow rate of 300 cm/h. The sample was eluted with elution buffer (sodium dihydrogen phosphate 0.3 g/L, disodium hydrogen phosphate 3.5 g/L, sodium chloride 5.84 g/L) to collect the rHSA-containing fractions. The electrophoretogram was shown in FIG. 3B.

3. Testing for Actual Loading Capacity of Q Sepharose FF

A 10/100 column was packed with about 5 ml of Q Sepharose FF media and equilibrated with 200 ml of equilibration buffer (sodium dihydrogen phosphate 0.3 g/L, disodium hydrogen phosphate 3.5 g/L, sodium hydroxide or hydrochloric acid was added to adjust the pH to 7.0) at a flow rate of 300 cm/h until the pH of the effluent was 7.0 and stable. 250 ml of the rHSA extract sample obtained in example 1 was adjusted to pH 7.5 and diluted with the buffer until the conductivity was less than 10.0 ms/cm and the total volume was 1000 ml. The sample was loaded on the Q Sepharose FF column at a flow rate of 300 cm/h. Absorption value of UV280 during the sample loading was recorded until the absorption value beyond plateau by 10%. The sample volume was recorded and the actual loading capacity per milliliter of Q Sepharose FF at a flow rate of 300 cm/h was calculated. Then the resin was regenerated.

Figure 4:
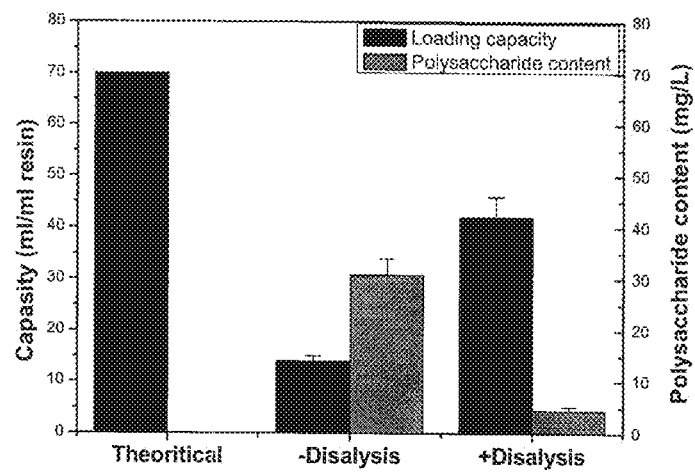
FIG. 4 is a change chart showing the loading capacity for the rHSA extract of Q Sepharose FF media and the content of polysaccharides in the rHSA extract pre or after dialysis.

The rHSA extract sample obtained in example 1 was adjusted to pH 7.0 and diluted with the buffer until the conductivity was less than 10.0 ms and then concentrated to 400 ml via GE 30KD membrane cassette. Sulphuric acid-phenol method was used to determine the content of polysaccharides before and after dialysis. Then the sample was loaded on an equilibrated Q Sepharose FF column. Absorption value of UV280 during the sample loading was recorded until the absorption value beyond plateau by 10%. The sample volume was recorded and the actual loading capacity per milliliter of Q Sepharose FF at a flow rate of 300 cm/h was calculated. The change of loading capacity and the change of the content of polysaccharides were shown in FIG. 4.

Example 4: Anion Exchange Chromatography as Secondary Purification

The rHSA-containing fraction obtained in example 2 was divided into two equal parts for use in the following experiments.

1. Anion Exchange Chromatography Performed on Q Sepharose FF Media

Figure 5:
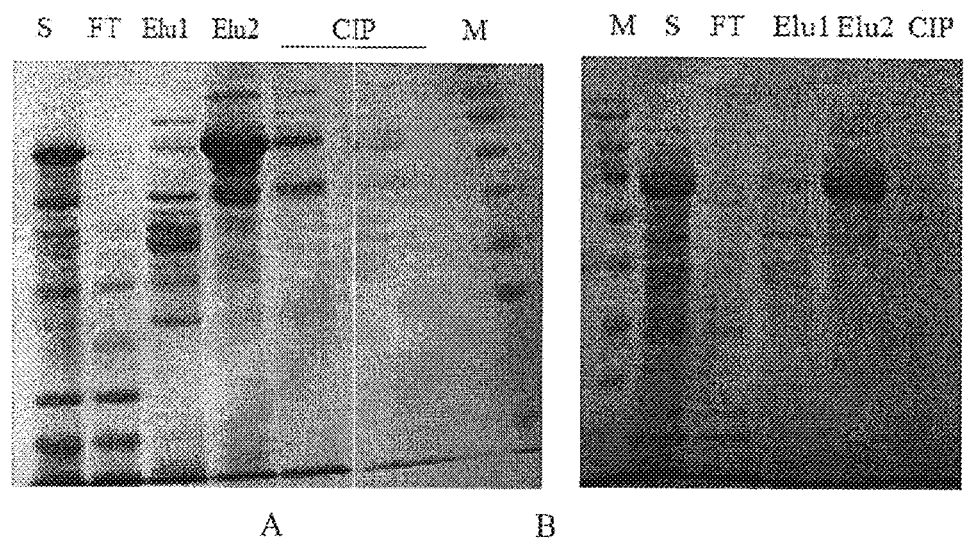
FIG. 5 is an image of SDS-PAGE of fractions obtained by anion exchange chromatography performed on different chromatography media as secondary purification, wherein A: Q Sepharose FFmedia, B: DEAE sepharose FF media.

A 15/200 column was packed with about 7 ml of Q Sepharose FF and equilibrated with 200 ml of equilibtration buffer (sodium dihydrogen phosphate 0.3 g/L, disodium hydrogen phosphate 3.5 g/L, sodium hydroxide or hydrochloric acid was added to adjust the pH to 7.0) at a flow rate of 300 cm/h until the pH of the effluent was 7.0. One part of the above fraction was adjusted to pH 7.0 and diluted with the buffer until the conductivity was less than 10.0 ms. The sample was loaded on the Q Sepharose FF column at a flow rate of 300 cm/h and then eluted with elution buffer (sodium dihydrogen phosphate 0.3 g/L, disodium hydrogen phosphate 3.5 g/L, sodium chloride 11.68 g/L) to collect the rHSA-containing fractions. The electrophoretogram was shown in FIG. 5A.

2. Anion Exchange Chromatography Performed on DEAE Sepharose FF Media

A Biological 15/200 column was packed with about 8 ml of DEAE Sepharose FF and equilibrated with 200 ml of equilibration buffer (sodium dihydrogen phosphate 0.3 g/L, disodium hydrogen phosphate 3.5 g/L, with sodium hydroxide or hydrochloric acid added to adjust the pH to 7.0) at a flow rate of 300 cm/h until the pH of the effluent was 7.0. Another part of the above fraction was adjusted to pH 7.5 and diluted with the buffer until the conductivity was less than 10.0 ms. The sample was loaded on to the DEAE Sepharose FF column at a flow rate of 300 cm/h and then eluted with elution buffer (sodium dihydrogen phosphate 0.3 g/L, disodium hydrogen phosphate 3.5 g/L, sodium chloride 11.68 g/L) to collect the rHSA-containing fractions. The electrophoretogram was shown in FIG. 5B.

Example 5: Hydrophobic Chromatography as Final Purification

1. Hydrophobic Chromatography Performed on Phenyl Sepharose HP Media

Figure 6:
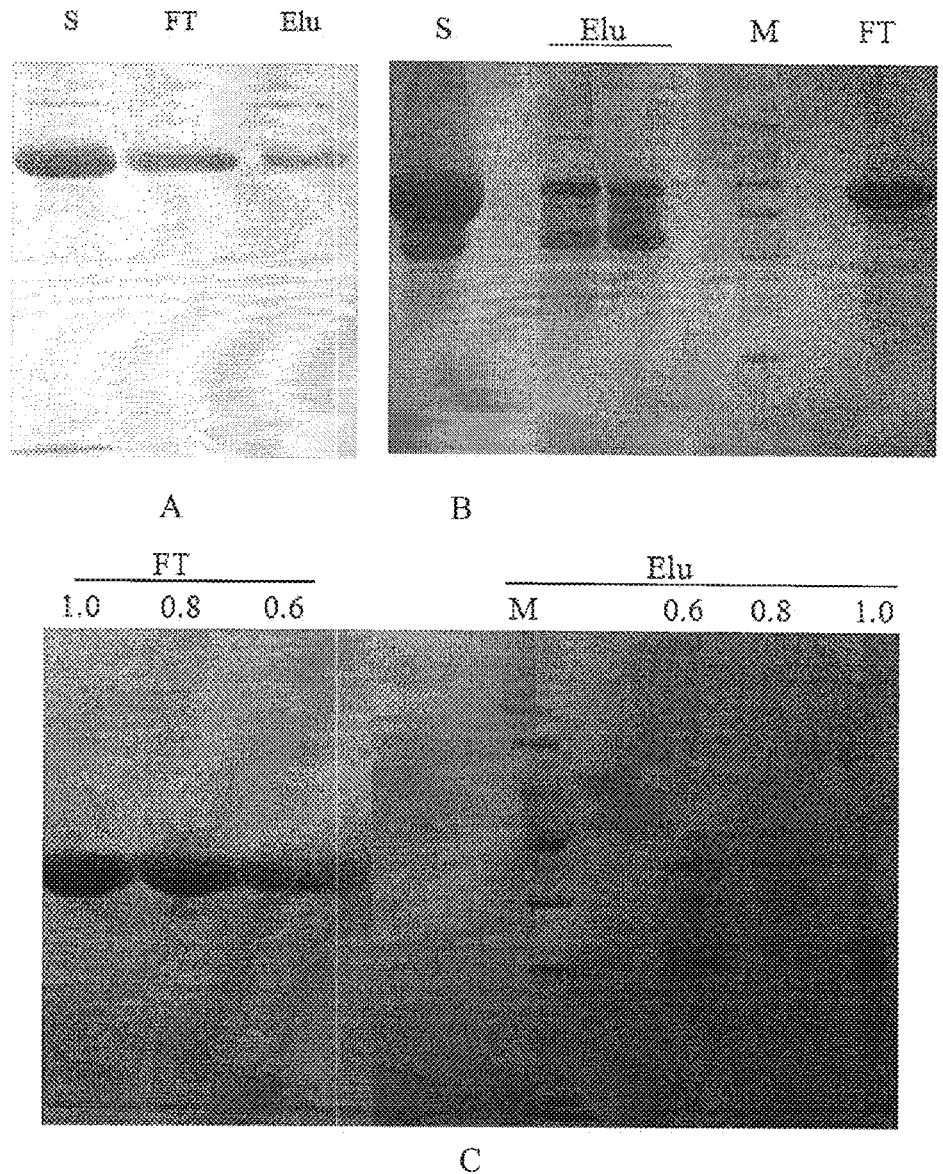
FIG. 6 is an image of SDS-PAGE of fractions obtained by hydrophobic chromatography performed on different chromatography media as final purification, wherein A: Phenyl Sepharose HP media, B: Phenyl Sepharose FF media, C: Macro Prep-t-Butyl media.

A XK16/100 column was packed with about 8 ml of Phenyl sepharose HP and equilibrated with 200 ml of equilibration buffer (anhydrous sodium acetate 2.32 g/L, sodium dihydrogen phosphate 2.81 g/L, ammonium sulfate 66 g/L) at a flow rate of 100 cm/h. 20 ml of the rHSA-containing fraction obtained in example 4 (Q Sepharose FF) was added with ammonium sulfate (0.4M) to make the conductivity be 80.0 ms. Then the sample was loaded on the column at a flow rate of 100 cm/h. The transmission fluid was collected to obtain the rHSA-containing fractions. The electrophoretogram was shown in FIG. 6A.

2. Hydrophobic Chromatography Performed on Phenyl Sepharose FF Media

A XK16/100 column was packed with about 10 ml of Phenyl sepharose FF and equilibrated with 200 ml of equilibration buffer (anhydrous sodium acetate 2.32 g/L, sodium dihydrogen phosphate 2.81 g/L, ammonium sulfate 13.2 g/L) at a flow rate of 150 cm/h. 20 ml of the rHSA-containing fraction obtained in example 4 (Q Sepharose FF)

was added with ammonium sulfate (0.1M) to make the conductivity be 80.0 ms. Then the sample was applied to the column at a flow rate of 150 cm/h. The transmission fluid was collected to obtain the rHSA-containing fractions. The electrophoretogram was shown in FIG. 6B.

3. Hydrophobic Chromatography Performed on Macro-Prep-t-Butyl Media

A 15/200 column was packed with about 6 ml of MacroPrep-t-Butyl and equilibrated with 200 ml of equilibration buffer (anhydrous sodium acetate 2.32 g/L, sodium dihydrogen phosphate 2.81 g/L, ammonium sulfate 13.2 g/L) at a flow rate of 150 cm/h. 20 ml of the rHSA-containing fraction obtained in example 3 (Q Sepharose FF) was added with ammonium sulfate (1.0 M, 0.8 M, 0.6M, respectively) to make the conductivity be 130.0 ms, 90.0 ms, 70.0 ms, respectively. Then the samples were applied to the columns at a flow rate of 150 cm/h. The transmission fluid was collected to obtain the rHSA-containing fractions. The electrophoretogram was shown in FIG. 6C.

Example 6: Separation and Purification of rHSA from the rHSA-Containing Extract

Figure 7:
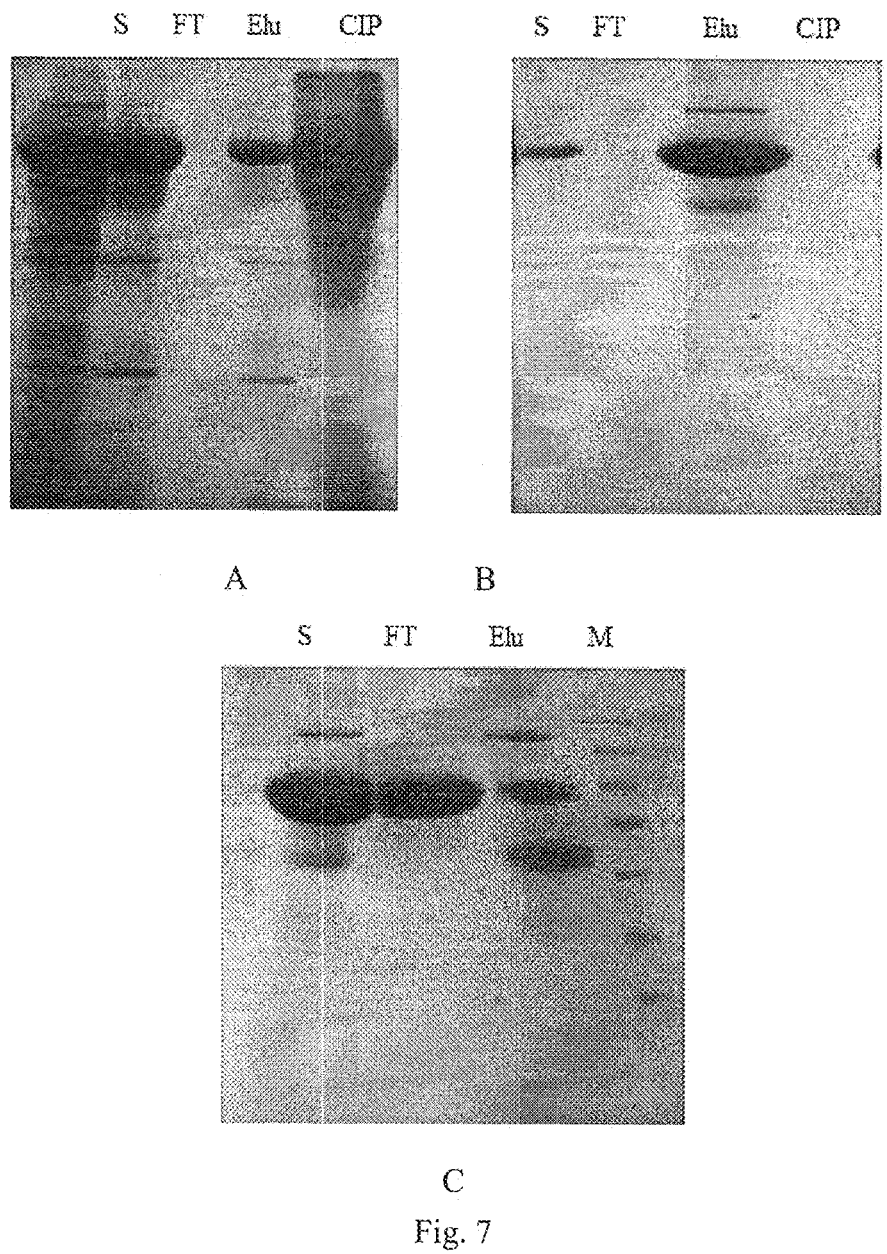
FIG. 7 is an image of SDS-PAGE of eluate fractions obtained by sequentially subjecting crude rHSA extract to cation exchange chromatography, anion exchange chromatography and hydrophobic chromatography, performed on UNOsphere S(A), Q Sepharose FF(B) and Phenyl Sepharose HP(C) as chromatography media, respectively.

Step 1): Cation Exchange Chromatography Performed on UNO Sphere S as Primary Purification An XK16/20 column was packed with about 12 ml of UNO Sphere S media and equilibrated with 500 ml of equilibration buffer (anhydrous sodium acetate 2 g/L, acetic acid, pH 4.5) at a flow rate of 300 cm/h. 300 ml of the rHSA-containing extract sample obtained in example 1 was loaded on the column at a flow rate of 600 cm/h. The sample has a conductivity of 6.5 ms/cm and a pH of 4.5. After loading, the sample was eluted with elution buffer (sodium acetate 2 g/L, acetic acid, pH 5.0, sodium chloride 14.61 g/L) at a flow rate of 200 cm/h. The eluate were collected and observed by SDS-PAGE to obtain the fractions containing rHSA. The electrophoretogram was shown in FIG. 7A.

Step 2): Anion Exchange Chromatography Performed on Q Sepharose FF as Secondary Purification An XK16/100 column was packed with about 13 ml of Q Sepharose FF media and equilibrated with 400 ml of equilibration buffer (anhydrous sodium acetate 6.51 g/L, sodium dihydrogen phosphate 0.72 g/L, pH 6.8) at a flow rate of 300 cm/h. The rHSA-containing fraction obtained in the previous step was diluted to about 200 ml with a conductivity of less than 10.0 ms and then loaded on the column at a flow rate of 300 cm/h. The sample had a conductivity of 8.3 ms/cm and a pH of 6.8. After loading, the sample was eluted with elution buffer (disodium hydrogen phosphate 6.51 g/L, sodium dihydrogen phosphate 0.72 g/L, sodium chloride 11.69 g/L) at a flow rate of 100 cm/h. The eluate were collected and observed by SDS-PAGE. The rHSA-containing fractions were collected. The electrophoretogram was shown in FIG. 7B.

Figure 8:
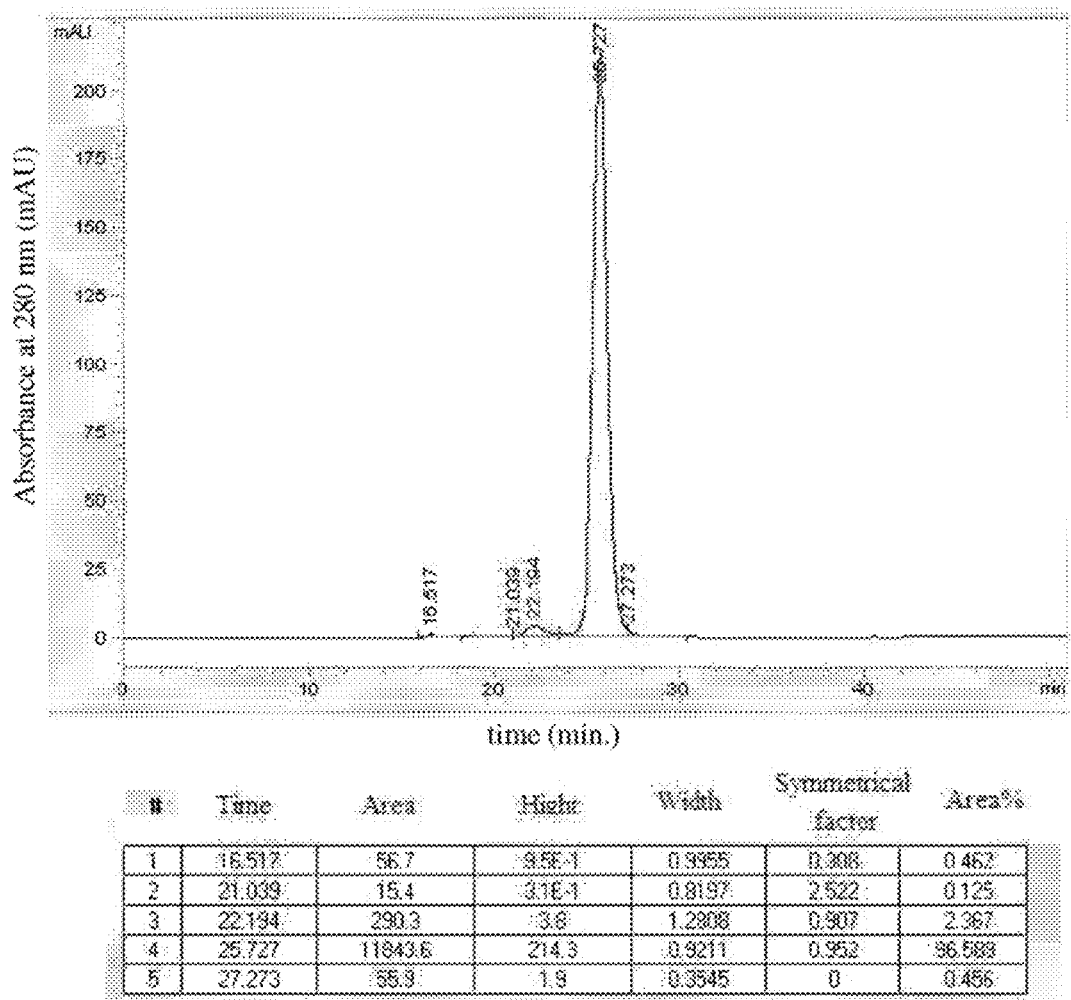
FIG. 8 is an HPLC chromatogram of the purified rHSA product (HPLC-SEC) obtained according to one embodiment of the present invention.

Step 3): Hydrophobic Chromatography Performed on Phenyl Sepharose HP as Final Purification An XK16/100 column was packed with about 12 ml of Phenyl sepharose HP and equilibrated with 200 ml of equilibration buffer (anhydrous sodium acetate 2.32 g/L, sodium dihydrogen phosphate 2.81 g/L, ammonium sulfate 66 g/L) at a flow rate of 100 cm/h. 20 ml of the rHSA-containing fraction obtained in the previous step was added with ammonium sulfate to make the conductivity be 90.0 ms. Then the sample was loaded on the column at a flow rate of 100 cm/h. The transmission fluid was collected to obtain the rHSA-containing fractions. The electrophoretogram was shown in FIG. 7C. The HPLC chromatogram of the purified rHSA product was shown in FIG. 8. The rHSA has a purity of more than 99% (monomer plus dimer and polymer) by HPLC.

Example 7: Separation and Purification of rHSA from the rHSA-Containing Extract

This example employs a four-step method to separate and purify rHSA by sequentially subjecting crude rHSA extract from Example 1 to cation exchange chromatography, anion exchange chromatography, ceramic hydroxyapatite chromatography and hydrophobic chromatography, performed on UNOsphere S, Q Sepharose FF, Macro-prep Ceramic hydroxyapatite Type I and Phenyl Sepharose HP as chromatography media, respectively. The cation exchange chromatography and anion exchange chromatography herein are the same as that of Example 6.

Figure 9:
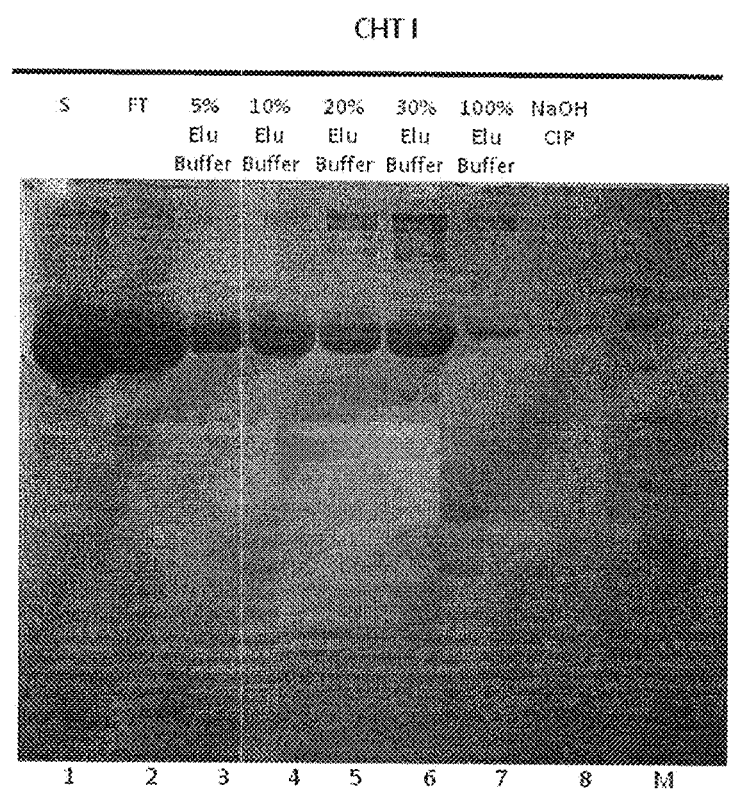
FIG. 9 is an image of SDS-PAGE of eluate fractions obtained by performing ceramic hydroxyapatite chromatography on Macro-prep Ceramic hydroxyapatite Type I media.

A CHT column was packed with about 15 ml of Macroprep ceramic hydroxyapatite type I media and equilibrated with 200 ml of equilibration buffer (20 mM sodium phosphate+50 mM sodium chloride, pH 7.5) at a flow rate of 100 cm/h. The rHSA-containing fraction obtained from anion exchange chromatography was directly loaded onto the column at a flow rate of 100 cm/h. The sample had a conductivity of 26 ms/cm and a pH of 7.4~7.6. After loading, the sample was eluted with an elution buffer (500 mM sodium phosphate, pH 7.5). The transmission fluid was collected to obtain the rHSA-containing fraction. The rHSA purification capacity was estimated to be ≤30 mg/g CHT I and the recovery rate of rHSA was up to ≥80%. Lastly, the CHT ceramic hydroxyapatite column should be regenerated with 3≡column volume of 500 mM sodium ohosphate buffer at pH 7.0. The column can be sanitized in 1~2N NaOH and stored in 0.1N NaOH if desired. The electrophoretogram was shown in FIG. 9.

Figure 10:
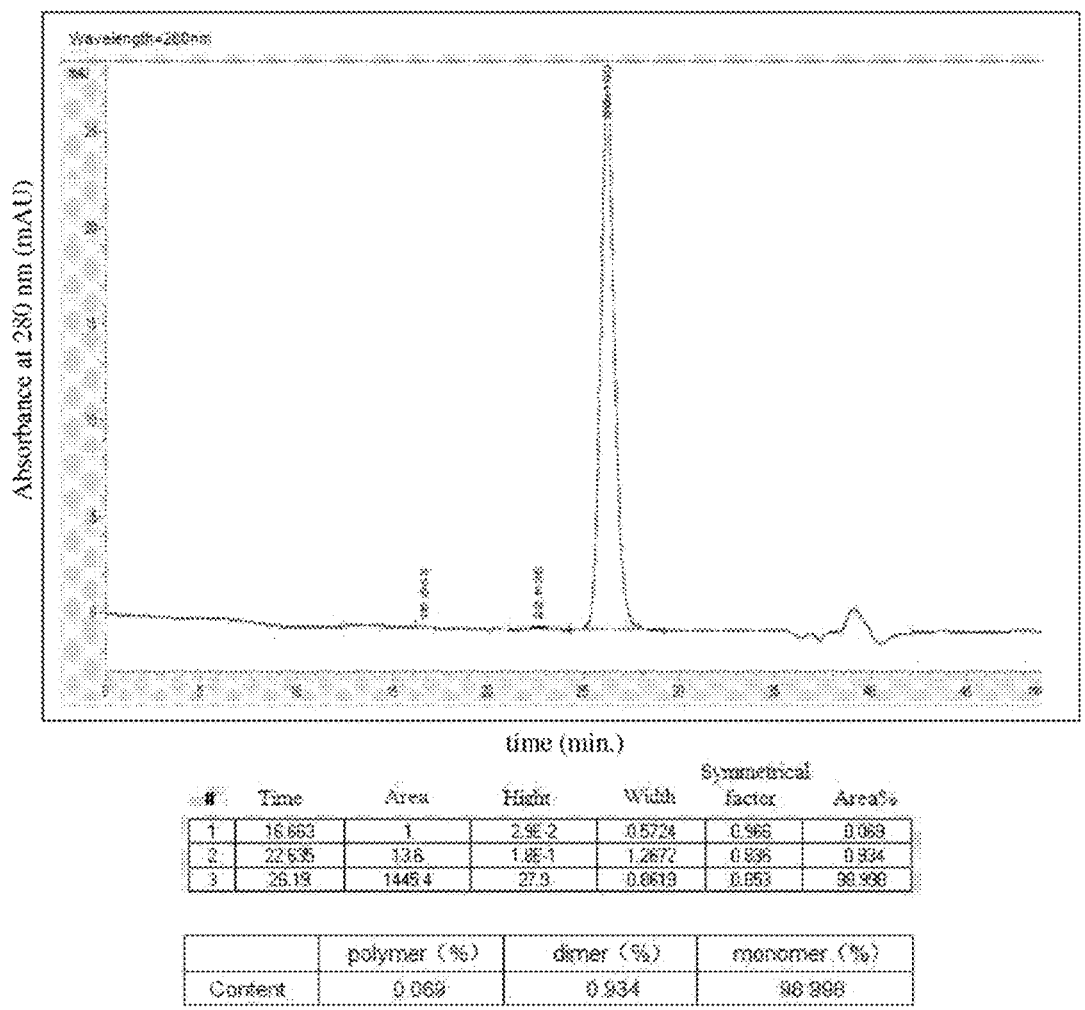
FIG. 10 is an HPLC chromatogram of the purified rHSA product obtained according to another embodiment of the present invention.

Then, the rHSA-containing fraction obtained above was subjected to hydrophobic chromatography according to the procedure similar to Example 6. The transmission fluid was collected to obtain the rHSA-containing fraction. The HPLC chromatogram of the purified rHSA product was shown in FIG. 10. The rHSA has a purity of about 99% (only monomer) by HPLC.

Example 8: Separation and Purification of rHSA from the rHSA-Containing Extract

The example was carried out by the same method as Example 7 except that the ceramic hydroxyapatite chromatography was performed on Macro-prep Ceramic hydroxyapatite Type II as chromatography media.

Figure 11:
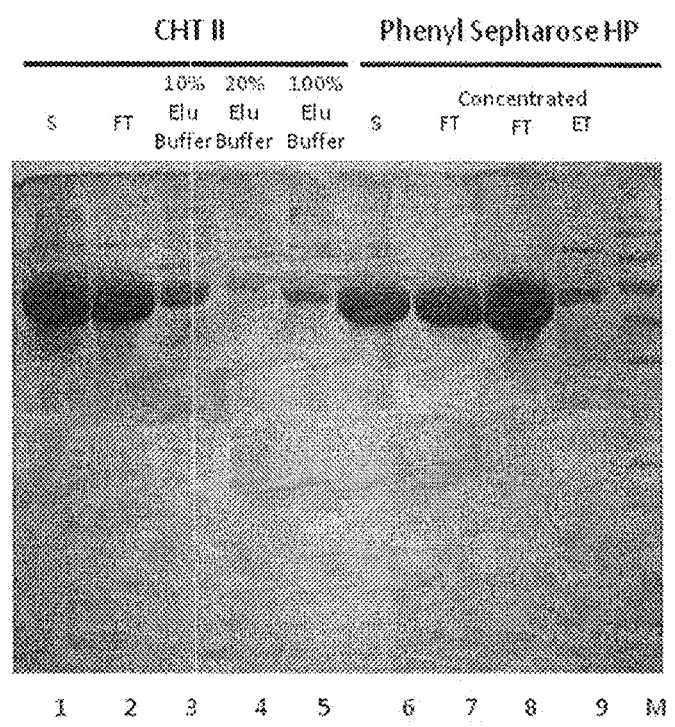
FIG. 11 is an image of SDS-PAGE of eluate fractions obtained by sequentially performing ceramic hydroxyapatite chromatography on Macro-prep Ceramic hydroxyapatite Type II media and hydrophobic chromatography on Phenyl Sepharose HP media.
Figure 12:
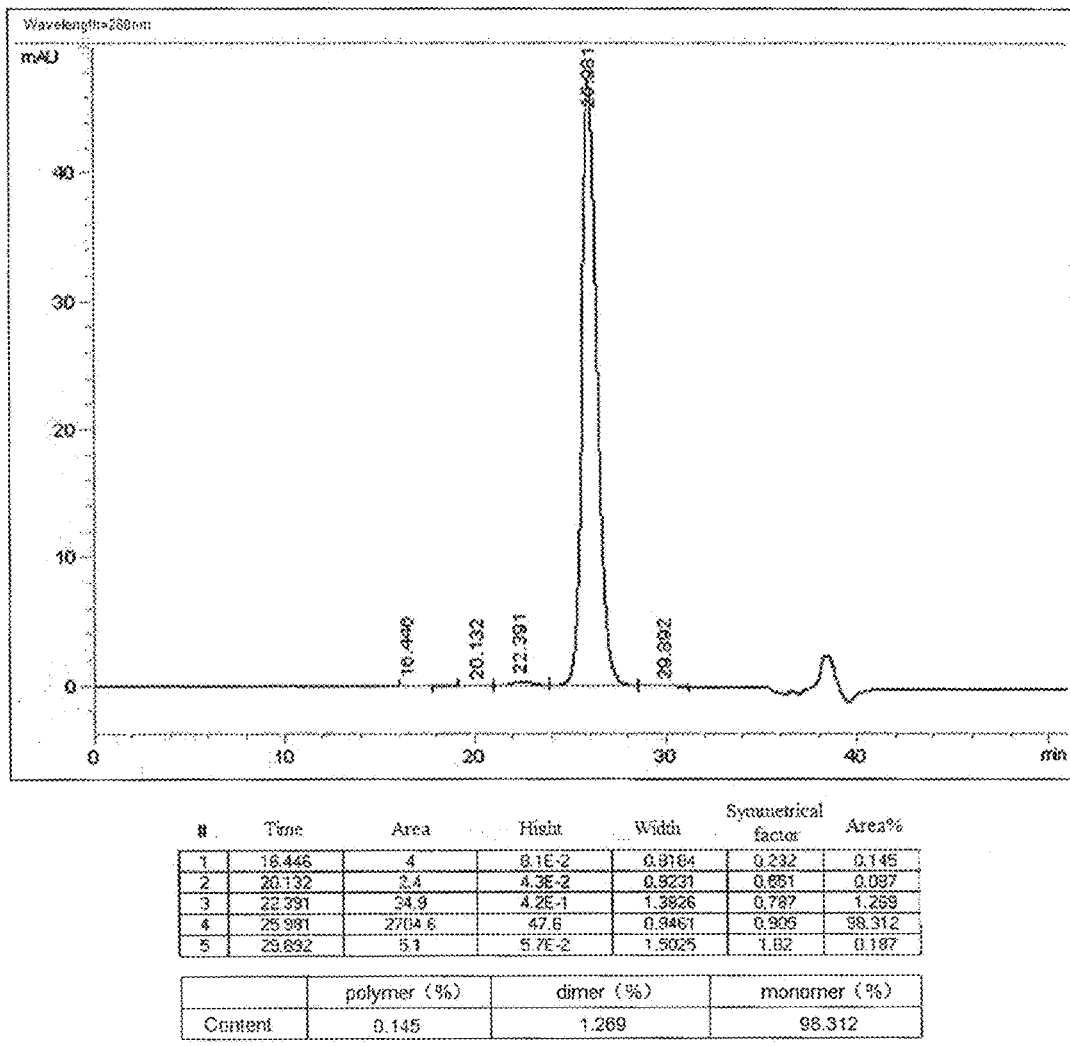
FIG. 12 is an HPLC chromatogram of the purified rHSA product obtained according to another embodiment of the present invention.

A CHT column was packed with about 15 ml of Macroprep ceramic hydroxyapatite type II media and equilibrated with 200 ml of equilibration buffer (20 mM sodium phosphate+50 mM sodium chloride, pH 7.0) at a flow rate of 100 cm/h. The rHSA-containing fraction obtained from anion exchange chromatography was directly loaded onto the column at a flow rate of 100 cm/h. The sample had a conductivity of 26 ms/cm and a pH of 7.4~7.6. After loading, the sample was eluted with an elution buffer (500 mM sodium phosphate, pH 7.0). The transmission fluid was collected to obtain the rHSA-containing fraction. The rHSA purification capacity was estimated to be ≤25 mg/g CHT II and the recovery rate of rHSA was up to ≥85%. Lastly, the CHT ceramic hydroxyapatite column should be regenerated with 3~5 column volume of 500 mM sodium ohosphate buffer at pH 7.0. The column can be sanitized in 1~2N NaOH and stored in 0.1N NaOH if desired. Then, the rHSA-containing fraction obtained from the previous step was subjected to hydrophobic chromatography according to the procedure similar to Example 7. The transmission fluid was collected to obtain the rHSA-containing fraction. The electrophoretogram was shown in FIG. 11. The HPLC chromatogram of the purified rHSA product was shown in FIG. 12. The rHSA has a purity of about 99% (only monomer) by HPLC.

It can be seen from the results of Examples 6~8 that the ceramic hydroxyapatite chromatography increases the monomer contents in final rHSA product effectively, allowing it to be up to about 99% purity. Further, the ceramic hydroxyapatite chromatography is simply operated because it used the flow-through way for further purified rHSA as the same as the way used in Phenyl sepharose HP step and the elutant solution is compatible without adjusting salt concentration and pH value. By ceramic hydroxyapatite chromatography, the purified rHSA can meet requirements for clinical application.

What is claimed is:

1. A method for isolating and purifying recombinant human serum albumin (rHSA) from transgenic rice grain, sequentially comprising the steps of:
   1) subjecting a crude extract from the transgenic rice grain containing the recombinant human serum albumin to cation exchange chromatography to obtain primary product I;
   2) subjecting the primary product I to anion exchange chromatography to obtain secondary product II that contains the recombinant human serum albumin, wherein the secondary product II further comprises ammonium sulfate at a concentration from about 0.1 M to about 1 M;
   3) subjecting the secondary product II to hydrophobic chromatography, under a condition that the rHSA does not adsorb to the resins of the hydrophobic chromatography; and
   4) recovering non-adsorbed flow-through fractions from the hydrophobic chromatography to obtain the purified recombinant human serum albumin having a purity of more than about 99% rHSA monomer plus dimer and polymer by HPLC.

2. The method according to claim 1, further comprising a step of subjecting the secondary product II to ceramic hydroxyapatite chromatography prior to the hydrophobic chromatography of step 3).

3. The method according to claim 2, wherein the ceramic hydroxyapatite chromatography is performed on a chromatography media selected from Macro-prep Ceramic hydroxyapatite Type I and Type II media.

4. The method according to claim 3, wherein the ceramic hydroxyapatite chromatography employs an elution buffer comprising a phosphate buffer with a pH of 7.0-7.5.

5. The method according to claim 2, wherein the purified recombinant human serum albumin has a purity of about 99% rHSA monomer by HPLC.

6. The method according to claim 1, wherein the cation exchange chromatography is performed on a chromatography media selected from the group consisting of UNOsphere S, Capto MMC, Nuvia S and MacroPrep-CM.

7. The method according to claim 6, wherein the cation exchange chromatography is performed on UNOsphere S or Capto MMC.

8. The method according to claim 6, wherein the cation exchange chromatography is performed on UNOsphere S and employs an elution buffer comprising acetate buffer, 0.25 M sodium chloride, with a pH of 5.2.

9. The method according to claim 6, wherein the cation exchange chromatography is performed on Nuvia S and employs an elution buffer comprising acetate buffer, 0.25 M sodium chloride, with a pH of 5.0.

10. The method according to claim 6, wherein the cation exchange chromatography is performed on Capto MMC, and employs a washing buffer comprising acetate buffer, 1 M sodium chloride, with a pH of 4.7 to remove non-target proteins, and an elution buffer comprising acetate buffer, 1 M sodium chloride, with a pH of 6.7 to elute the recombinant human serum albumin.

11. The method according to claim 6, wherein the cation exchange chromatography is performed on MacroPrep-CM, and employs a washing buffer comprising acetate buffer, 1 M sodium chloride, with a pH of 4.7 to remove non-target proteins, and an elution buffer comprising acetate buffer, 1 M sodium chloride, with a pH of 6.5 to elute the recombinant human serum albumin.

12. The method according to claim 1, wherein the anion exchange chromatography is performed on a chromatography media selected from the group consisting of Q Sepharose FF, UNOsphere Q and DEAE Sepharose FF.

13. The method according to claim 12, wherein the anion exchange chromatography is performed on Q Sepharose FF.

14. The method according to claim 12, wherein the anion exchange chromatography is performed on Q Sepharose FF and employs an elution buffer comprising a phosphate buffer, 0.25 M sodium chloride, with a pH of 6.0-7.0.

15. The method according to claim 12, wherein the anion exchange chromatography is performed on DEAE Sepharose FF, and employs a washing buffer comprising phosphate buffer, 0.1 M sodium chloride with a pH of 6.0-7.0 to remove non-target proteins, and an elution buffer comprising a phosphate buffer, 0.25 M sodium chloride, with a pH of 6.0-7.0 to elute the recombinant human serum albumin.

16. The method according to claim 1, wherein the hydrophobic chromatography is performed on a chromatography media selected from the group consisting of Phenyl Sepharose HP, Phenyl Sepharose FF, macro-prep t-butyl and macro-prep methyl.

17. The method according to claim 16, wherein the hydrophobic chromatography is performed on Phenyl Sepharose HP.

18. The method according to claim 16, wherein the hydrophobic chromatography is performed on Phenyl Sepharose HP, and the secondary product II is adjusted to 0.4 M ammonium sulfate prior to the hydrophobic chromatography step.

19. The method according to claim 16, wherein the hydrophobic chromatography is performed on Phenyl Sepharose FF, and the secondary product II is adjusted to 0.1 M ammonium sulfate prior to the hydrophobic chromatography step.

20. The method according to claim 16, wherein the hydrophobic chromatography is performed on MacroPrep-t-Butyl, and the secondary product II is adjusted to 0.6-1.0 M ammonium sulfate prior to the hydrophobic chromatography step.

21. The method according to claim 1, wherein said crude extract of the recombinant human serum albumin is prepared by a method comprising the steps of:
   i) mixing milled transgenic rice grain containing the recombinant human serum albumin with an extraction buffer in a w/v (kg/L) ratio of 1:5 and extracting at 55-60° C. for 1-1.5 hours to obtain mixture I; said extraction buffer comprising 10-30 mM phosphate buffer, 10-20 mM sodium acetate, 15-30 mM ammonium sulfate and 5-20 mM sodium caprylate, with a pH of 6.5-8;

ii) adjusting the pH of mixture I of step i) to 4.0-4.5 and precipitating it for 3-12 hours to obtain mixture II;

iii) filtrating the mixture II of step ii) and collecting the filtrate to obtain a crude extract containing high concentration of recombinant human serum albumin; said filtrating comprising steps of filtrating by pressure filtration with a filter cloth type plate-frame filter, then filtrating by micro-filtration with a polyethersulfone hollow fiber membrane with a pore size of 0.20 µm-0.45 µm.

22. The method according to claim 1, wherein the cation exchange chromatography employs a loading buffer comprising an acetate buffer with a pH less than 5.0.

23. The method according to claim 1, wherein the cation exchange chromatography employs an elution buffer comprising an acetate buffer and sodium chloride, or a phosphate buffer and sodium chloride; with a pH of 5.0-6.7.

* * * * *